United States Patent [19]

King

[11] Patent Number: 5,750,790
[45] Date of Patent: May 12, 1998

[54] REDUCTIVE AMINATION CATALYSTS

[75] Inventor: Stephen Wayne King, Scott Depot, W. Va.

[73] Assignee: Union Carbide Chemicals & Plastics Technology Corporation, Danbury, Conn.

[21] Appl. No.: 567,832

[22] Filed: Dec. 6, 1995

Related U.S. Application Data

[62] Division of Ser. No. 171,823, Dec. 22, 1993, abandoned.

[51] Int. Cl.⁶ .................................................. C07C 209/70
[52] U.S. Cl. .................... 564/469; 502/300; 502/331; 502/335; 502/337; 502/345
[58] Field of Search ........................ 502/300, 331, 502/335, 337, 345; 564/480, 469

[56] References Cited

U.S. PATENT DOCUMENTS

| | | |
|---|---|---|
| 1,031,663 | 3/1912 | Junzio et al. |
| 4,123,462 | 10/1978 | Best. |
| 4,602,000 | 7/1986 | Dupin et al. .................. 502/335 |
| 4,912,260 | 3/1990 | Dobson et al. ................ 564/480 |
| 5,068,329 | 11/1991 | Burgess et al. ............... 544/402 |
| 5,202,490 | 4/1993 | Burgess et al. ............... 564/480 |
| 5,352,835 | 10/1994 | Dai et al. ..................... 502/331 |

FOREIGN PATENT DOCUMENTS

| | | |
|---|---|---|
| 1031663A | 3/1989 | China. |
| 1031699A | 3/1989 | China. |

*Primary Examiner*—Elizabeth D. Wood
*Attorney, Agent, or Firm*—J. B. Mauro

[57] ABSTRACT

The present invention relates to improved reductive amination catalysts useful in the production of alkyleneamine compositions having lower levels of cyclic components. Although typical reductive amination catalysts contain nickel or nickel-rhenium on carriers such as alumina, silica, silica-alumina and silica-titania, it has been discovered that by using carriers selected from the transitional aluminas, improvements are obtained in both selectivity to acyclic products and in activity of the catalysts.

8 Claims, No Drawings

REDUCTIVE AMINATION CATALYSTS

This application is a Division of prior U.S. application Ser. No. 08/171,823 filed on Dec. 22, 1993 and now abandoned.

BACKGROUND OF THE INVENTION

The present invention relates to improved reductive amination catalysts useful in the production of alkyleneamine compositions having lower levels of cyclic components. More specifically, the invention provides catalysts which are useful in the reductive amination of monoethanolamine and ammonia to produce product compositions having higher levels of acyclic products (e.g. ethylenediamine) and reduced levels of cyclic products (e.g. piperazine).

A significant portion of the ethylenediamine (EDA) made commercially is made by the continuous reaction of monoethanolamine (MEA) and ammonia in the presence of hydrogen over a fixed bed reductive amination catalyst.

A wide variety of reductive amination catalysts are known in the art for this reaction. Typically, these catalysts utilize nickel or nickel in combination with other metals such as rhenium to effect the reductive amination reaction. It is appreciated in the reductive amination art, that reductive amination catalysts must first be reduced before effecting the reaction, and then hydrogen gas employed during the course of the reaction in order to maintain catalytic activity and selectivity.

U.S. Pat. No. 4,123,462 describes a nickel-rhenium reductive amination catalyst for the production of desirable alkylamines and reduction of undesirable by-products having improved selectivity and increased conversion. The nickel-rhenium catalyst comprises rhenium and nickel impregnated on a support material selected from the group consisting of aluminas, silicas, silica-aluminas, kieselguhrs or diatomaceous earths and silica-titanias.

U.S. Pat. No. 4,912,260 describes reductive amination of an alcohol, aldehyde or a ketone with either ammonia or an amine or a nitrile in the presence of a catalyst composition comprising (i) nickel, (ii) ruthenium, and (iii) at least one other transition metal selected from either the second or third row transition metals, to give an amine product. The patent states that the catalyst composition is supported on a suitable support including aluminas, silicas, silica-aluminas, carbons and zeolites, of which gamma-alumina is a preferred support.

U.S. Pat. No. 5,068,329 describes a continuously generated alkyleneamines producers composition rich in AEEA prepared by the reaction of MEA in the presence of a reductive amination catalyst. The patent lists numerous known reductive amination catalysts useful in the process including those which typically contain metals such as nickel, rhodium, rhenium, zinc, palladium, platinum and the like carried on various materials such as alumina, silica, silica-alumina, kieselguhr, diatomaceous earth and silica-titania. The patent states that support materials are not equivalent in their ability to form active catalysts and that the actual effectiveness of a material as a carrier in a potentiated nickel catalyst is generally not predictable in advance. In addition, the nickel-rhenium catalyst disclosed can contain other metals in admixture with the nickel and rhenium which do not detrimentally affect the catalytic properties of the catalyst. It is stated that certain metals can extend the activity life and other physical properties of the Ni—Re catalysts, such as lanthanum, calcium, magnesium, strontium, lithium, potassium, barium, cesium, tungsten, iron, ruthenium, copper, silver, zinc, cobalt, uranium, titanium, boron and manganese.

U.S. Pat. No. 5,202,490 describes a process for the manufacture of an alkyleneamines reaction product mixture, without a net increase in piperazine, by the reaction of MEA and ammonia using a reductive amination catalyst. The patent describes the same catalysts enumerated above and in addition states that other preferred reduction amination catalysts are composed of rhenium, nickel and boron impregnated on a support material selected from the group consisting of alumina (e.g. alpha), silicas, silica-aluminas, kieselguhrs or diatomaceous earths and silica-titanias, wherein the ratio of nickel to boron to rhenium is in the range of from about 2:2:1 to about 30:30:1 and the total nickel, boron and rhenium present is in the range of about 3 to about 30 percent by weight of the carrier material.

Chinese Laid-Open Patent Application No. CN 1031699A describes a method of manufacturing high yields of morpholine compounds in the presence of hydrogen and an amination catalyst using dialkyl glycol, compounds containing carboxyl groups and ammonia as the raw materials. The catalysts comprise aluminum oxide and three or more metals selected from Ni, Cu, Cr, Ti and Re or mixtures thereof. One of the catalysts in the application is described as an active composition of gamma-alumina, theta-alumina or a mixture of both in any desired ratio loaded with Ni, Cu, Cr and/or Re. It is stated that by comparison to existing technologies, the method of the invention when used in amination reactions results in comparatively great increases in the conversion ratios of the raw materials and in selectivity for the morpholine compounds produced.

Methods of preparing the above catalysts is disclosed in Chinese Laid-Open Patent Application No. 1031663A, which describes an ammoniation reaction catalyst composed of an active composition of Ni, Cu, Cr and/or Re loaded on a carrier of delta-, theta- or (delta+theta) alumina in any desired proportion. The carrier is obtained from thin gibbsite by baking at 7500° to 920° C. for 2 to 8 hours. The percentage of carrier in the catalyst is 65 to 90, with the remainder being active components. The active components are present in ratios of Ni:Cu from 10:1 to 8:1, Ni:Cr from 1:0 to 5:1 and Ni:Re from 1000:1 to 100:1. It is stated that the catalyst of the invention can be widely used in various types of ammoniation reactions and is particularly suited for manufacturing fatty amines, morpholine and N-alkyl morpholine. In addition, the catalyst of the invention can also be used with fatty dihydric alcohol as the raw material to obtain five-member or six-member N-heterocyclic compounds such as piperazine and piperidine.

It would be beneficial to have catalysts which increase the ability to manufacture desirable acyclic products such as EDA, DETA and AEEA without generating large amounts of cyclic alkylenepolyamine products.

SUMMARY OF THE INVENTION

In accordance with the present invention, reductive amination catalysts are provided which allow for the manufacture of desirable products such as EDA, DETA and AEEA without generating large amounts of cyclic products such as PIP, AEP and HEP.

Although typical reductive amination catalysts contain nickel or nickel-rhenium on carriers such as alumina, silica, silica-alumina and silica-titania, it has been unexpectedly found that by using carriers selected from the transitional aluminas, improvements are obtained in both selectivity, and in some cases activity.

According to a preferred embodiment of the present invention, there are provided reduction amination catalysts having high activity and selectivity to the production of EDA, DETA and AEEA while minimizing PIP and other cyclic by-products, said catalysts comprising reductive amination metals, such as nickel and rhenium, incorporated with carrier materials selected from transitional aluminas including delta and theta aluminas and mixed phases such as gamma-theta, delta-theta, or theta-alpha aluminas; or mixtures thereof.

When using the transitional alumina carriers of the present invention to prepare nickel-rhenium reduction amination catalysts, it has been found that these carriers allow for use of reduced levels of rhenium.

It is an objective of this invention to provide reductive amination catalysts to effect the reaction of MEA in the presence of hydrogen and ammonia to produce EDA, DETA and AEEA as the principal products of the reaction.

accepted as the transitions when the starting material is coarse gibbsite in air: gibbsite→boehmite→gamma→delta→theta→alpha alumina Of the transitional aluminas described above, the delta and theta phases are preferred carriers for the process of the invention. Other preferred transitional aluminas include mixtures of transitional aluminas such as gamma-theta, delta-theta, theta-alpha phases or mixtures thereof.

Transitional alumina carriers may be characterized using an X-ray Diffractometer by methods known in the art. The following table lists the accepted 2-theta values for the transitional aluminas, as supplied by the Joint Committee on Powder Diffraction Standards International Center for X-Ray Diffraction, and several catalyst carriers of the present invention, as hereinafter described:

| Transitional Aluminas | | | | | | | | |
|---|---|---|---|---|---|---|---|---|
| gamma | 19.58 | 31.94 | 37.60 | 39.49 | 45.79 | 60.76 | 66.76 | |
| delta | 17.65 | 19.49 | 21.82 | 31.14 | 32.78 | 34.74 | 36.96 | 39.49 |
| | 45.55 | 46.54 | 47.57 | 50.67 | 60.03 | 61.35 | 62.26 | 64.18 |
| | 66.76 | 67.31 | 73.33 | 75.37 | | | | |
| theta | 15.5 | 16.25 | 19.54 | 31.509 | 32.778 | 34.939 | 36.743 | 38.871 |
| | 39.911 | 44.856 | 46.4242 | 47.5849 | 50.6803 | 51.3931 | 52.6308 | 54.5575 |
| | 56.7218 | 58.7033 | 61.2553 | 62.3387 | 64.0501 | 65.3714 | 67.4008 | |
| alpha | 25.5 | 35.4 | 38.0 | 43.6 | 52.8 | 57.6 | 63.05 | 66.7 |
| | 68.4 | | | | | | | |
| Cat. F | 39.4672 | 45.7691 | 46.0159 | 46.4638 | 46.8969 | 65.8291 | 66.4935 | 67.2831 |
| Cat. I | 31.2119 | 32.7897 | 36.7688 | 39.5019 | 39.7188 | 44.8422 | 66.5872 | 67.3378 |
| Cat. J | 19.6 | 25.5362 | 31.2322 | 32.7675 | 35.1091 | 36.6600 | 37.7275 | 38.9028 |
| | 39.8125 | 43.3084 | 44.7931 | 47.5881 | 52.5094 | 57.4538 | 66.4734 | 67.3944 |
| | 68.1550 | | | | | | | |
| Cat. L | 25.5075 | 35.0803 | 37.7012 | 43.2813 | 52.4825 | 57.4247 | 66.4453 | 68.1325 |

DESCRIPTION OF THE PREFERRED EMBODIMENTS

Processes for carrying out the reaction of MEA and ammonia in the presence of hydrogen are well known in the art. In general, the process may be effected by contacting, in a reactor containing a reductive amination catalyst, a feedstream of MEA, hydrogen and ammonia, typically in a mole ratio of ammonia to MEA of about 1 to about 30; where hydrogen comprises about 10 to about 50 mole percent of the feed. Water may also be provided in the feed at up to about 20 weight percent of the weight of MEA.

Preferred reductive amination catalysts for practice of the present invention include those prepared by incorporating at least one catalytically effective reductive amination metal on transitional alumina carriers. These preferred reductive amination catalysts provide a higher ratio of acyclic to cyclic products when compared to a similar catalyst not containing said transitional aluminas.

Transitional aluminas or activated aluminas are defined in Kirk-Othmer (Vol. 2, pp. 291, 1992) as a series of partially hydroxylated aluminum oxides (excluding alpha aluminas which are anhydrous in nature). In general, as a hydrous alumina precursor is heated, hydroxyl groups are driven off leaving a porous solid structure. As the activation temperature increases through the transitional phases, the crystal structures become more ordered thus allowing for identification of transitional aluminas by x-ray diffraction. The sequences of transition are affected not only by the starting materials but also by their coarseness of crystallinity, heating rates, and impurities. The following transitions are generally Although the crystallinity of alpha alumina is highly distinctive when compared to the transitional aluminas, in mixed phases which contain small amounts of alpha alumina, the amount of alpha alumina present is not easily quantified. However, due to the extremely low surface areas of alpha aluminas, useful mixed phases containing alpha alumina can be determined by those which fall within the surface area ranges described below.

Transitional aluminas are considered to be intermediate surface area carriers. The surface areas are preferably between about 10 m$^2$/gm and about 200 m$^2$/gm; more preferably between about 40 m$^2$/gm and about 180 m$^2$/gm; and most preferably between about 80 m$^2$/gm and about 140 m$^2$/gm.

The transitional alumina carriers used in making the catalyst may be of any convenient shape or size. The shape of the carrier usually will depend upon the shape required by the particular apparatus used to perform the reductive amination. Catalysts can be made on transitional alumina carriers in the form of powders, spherical pellets, extruded strips and the like. Impregnated spherical pellets ranging in diameter from about 0.3 cm to about 0.5 cm and extruded strips of a cylindrical-type shape ranging from about 0.8 mm to about 1.3 cm in length are typical of those which can be used as carriers.

The particular method of incorporating the transitional alumina carriers with reduction amination metals is insignificant to the activity or selectivity of the final catalyst in amination processes; however, impregnated catalysts generally perform better than precipitated catalysts.

One technique for impregnating the reductive amination metals onto the transitional alumina carrier is by incipient wetness techniques using salt solutions of the metals. Various organic and inorganic salts of metals may be used in impregnation solutions. The following description will be limited to the preferred reductive amination metals of the present invention, nickel, nickel and rhenium, or nickel, rhenium and boron salts. However, it is to be fully understood that the invention is not limited to the use of these metals and that other metals, typically used on reductive amination catalysts, may also be used in combination with the preferred transitional alumina carriers to obtain improved results. These metals include, for example, cobalt, rhodium, iridium, ruthenium, zinc, palladium, platinum and the like.

Examples of suitable nickel-containing salts are nickel nitrate hexahydrate, nickel formate and nickel acetate tetrahydrate and the like. Typical rhenium salts employed include ammonium perrhenate and perrhenic acid.

In preparing the salt solutions, the amount of total metal desired to be impregnated on a specific quantity of transitional alumina carrier and the relative atom ratio of nickel to rhenium should be considered as both factors have been found to affect the final properties of the catalysts.

Some active catalysts have been found to be those in which the nickel to rhenium atom ratio is between 1:1 and 30:1. In most previous patents, the maximum activity has been shown to occur when this ratio is between about 5:1 and 20:1. However, it has been unexpectedly found that by using the transitional alumina carriers of the present invention, the levels of rhenium can be significantly lowered while still maintaining high activity and selectivity. For example, in the present invention, the desired atom ratio of nickel to rhenium is typically in the range of from about 1:1 to about 200:1; more preferably from about 5:1 to about 100:1; and most preferably from about 10:1 to about 50:1. Although there may be some decrease in selectivity at the higher ratios, these catalysts containing lower levels of rhenium are still active catalysts.

The total amount of reductive amination metals to be impregnated onto the transitional alumina carrier also has an effect on the activity of the catalyst. The total metal content is preferably in the range of from about 1 to 30% by weight of the carrier; more preferably from about 5% to about 15%.

Where relatively large amounts of metal are to be impregnated on carriers, a single impregnation step may not be sufficient. Although an impregnation solution may be prepared with the minimum amount of solvent required to dissolve the metal salts, the total amount of the impregnation solution may be greater than that which the carrier can absorb. In such case, a portion of the impregnation solution less than the maximum absorption amount is used to initially contact the carrier. After contacting, the carrier is dried and then contacted with an additional amount of impregnation solution. These sequential steps of contacting with solution and drying are continued until all of the impregnation solution is used. A typical drying step can comprise heating the impregnated carrier to a temperature of 120° C. for several hours. Evacuation drying may also be used, where the carrier is cooled under reduced pressure, or the material may be calcined at elevated temperatures ($\geqq$300° C.) to decompose the salt to the metal oxide.

It may also be advantageous to dry the transitional alumina carriers prior to impregnation in order to ensure that the carrier will take up as much of the solution as possible. This pre-drying step enables the metal to permeate more deeply into the carrier during impregnation. The penetration of the metal into the transitional alumina carrier may be further increased by techniques known to those skilled in the art, such as by increasing the time the carrier is in contact with the solution. Other impregnation techniques are well known in the art and may be utilized in the present invention.

After the transitional alumina carrier is impregnated with the desired amount of metal(s), it is completely dried and then activated by a reduction step. The drying step is any technique which sufficiently evaporates the volatile constituents of the impregnating solution, such as by heating the catalyst to a temperature of about 120° C. under inert atmospheres, e.g. in the presence of nitrogen, followed by cooling under reduced pressure.

The catalyst may then be activated, preferably by contacting the catalyst with a hydrogen atmosphere at an elevated temperature of from about 200° C. to about 600° C. for periods of from about 45 minutes to about 4 hours. The reduced catalyst is best handled in the absence of air in order to maintain optimal performance and prevent pyrophoric behavior. The catalyst may be stabilized by gentle oxidation, carbon dioxide treatment, or other conventional techniques for stabilizing pyrophoric catalysts, and may then be handled in air prior to its utilization. The catalyst is then activated in a separate step or in situ. The specific conditions for reduction of the catalysts are dependent upon the particular catalyst composition being activated, as is known in the art.

Prior to the activation step, the catalyst may be optionally calcined. In a preferred calcining step, the catalyst is heated to temperatures in the range of from about 300° C. to about 550° C. for one minute to about 3 hours or more. It is preferred that the calcining step be carried out in air. The drying step referred to above may be replaced by the calcining step or activating step.

The amount of Ni—Re catalyst present in the process of the invention depends on many variables including the relative proportions of the reactants, reaction conditions and degree of conversion and selectivity desired. Moreover, the amount of catalyst will depend also on the nature of the catalyst itself, e.g., its metal loading and activity. The catalyst should be present in the reaction zone in sufficient catalytic amount to enable the desired reaction to occur.

Preferred reductive amination catalysts are catalysts composed of nickel and rhenium or nickel, rhenium and boron impregnated on a transitional alumina carrier, preferably on a delta or theta phase transitional alumina, including mixed phases such as gamma-theta, delta-theta, theta-alpha phases or mixtures thereof; wherein the atom ratio of nickel to rhenium is in the range of from about 10:1 to about 50:1; and the total amount of nickel and rhenium present is in the range of from about 5 to about 15 percent by weight of the transitional alumina carrier. When boron is present as an additional component, typical atom ratios of nickel to boron are from about 0.1 to about 6.0

The process of the invention is not limited to a confining set of conditions. The feed stream may be liquid, supercritical fluid or gaseous, and the reaction product stream taken from the reaction zone may be liquid, supercritical fluid or gaseous. It is not necessary that the feed stream and the reaction product stream be in the same physical state.

The reactor design is also not narrowly critical. The feed thereto may be upflowing or downflowing, and design features in the reactor which optimize plug flow in the reactor may be employed.

The reactants may be fed as a stream, typically continuously, to the bed of the catalyst. The catalyst is usually a fixed bed of solid particles (pellets, tablets, extrudates, spheres, etc.) which comprise the catalyst deposited on the preferred transitional alumina carriers, as described above. The reaction occurs in the bed and thus the bed defines the reaction zone. The effluent from the bed or the reaction zone is also a stream comprising the unreacted components of the feed stream and the principal reaction products EDA, DETA and AEEA, plus a number of other amine compounds.

The conditions for reaction are also not narrowly limited. For example, the pressures for carrying out the process may range from about 1000 psig to about 3000 psig, more preferably from about 1200 psig to about 2200 psig. In addition, the process may typically be carried out at temperatures from about 120° C. to about 300° C, preferably from about 140° C. to about 200° C.

The following examples are intended for the purpose of illustrating this invention and not for the purpose of limiting it. In order to make direct comparisons of the various catalysts evaluated, a specific set of reaction conditions was chosen. As is well known in the art, the product mixtures of any reaction process can be changed by varying such things as the feed mole ratio of reactants, product recycle, feed space velocity, hydrogen concentration, time on organics, temperature and the like. The selection of these operating variables is dependent on the desired conversions and product selectivity.

EXAMPLES

In the examples set forth in the tables below, the catalyst of choice is placed in a tubular reactor having an outside diameter of about 2.54 cm and an overall length of about 76 cm. The catalyst portion of the reactor comprises a length of about 61 cm, capable of accommodating about 150 cubic centimeters of catalyst. The reactor is made of 316 stainless steel.

For each of the examples, the tubular reaction system is brought to the designated conditions, ammonia and MEA are premixed to the appropriate feed mole ratio and then pressure fed to the system. The liquid feed is then mixed with hydrogen and this mixture passed to a preheater prior to entering the reaction zone.

The reaction mixture is passed through the reaction zone in a downflow fashion. The pressure in the reaction zone is controlled by a motor valve at the outlet of the reactor. After leaving the reaction zone, the pressure of the stream is reduced from that of the reaction zone to slightly above atmospheric. This stream is then passed through a trap where hydrogen is separated from the condensables which are collected in a semi-batch fashion. The condensable sample, which contains unreacted ammonia and MEA and the products of the reaction, is then analyzed for water by a Karl-Fisher procedure and for organics (amines) by capillary gas chromatography.

Catalysts are generally prepared by using the incipient wetness technique with multiple impregnations, and calcinations in air after each impregnation step. The impregnated carrier is then reduced in a Lindberg furnace equipped with an Iveron Pacific Model 2300A programmable setpoint controller at a temperature of 340° C. over a period of about 5 hours. The catalysts are activated at 180° C. overnight under hydrogen after charging to the reactor described above. A 10:1 molar ratio of ammonia:MEA, is then feed to the reactor as the liquid feed in the presence of hydrogen.

The catalysts and/or carriers employed in the examples hereinafter were obtained from Norton Company, Akron, Ohio and United Catalysts, Inc. The following materials were purchased and used in preparing the catalysts, without further purification: nickel nitrate hexahydrate (Fisher), nickel acetate tetrahydrate (Aldrich), ammonium hydroxide (Baker), ammonium perrhenate (Strem), and orthoboric acid (Johnson Matthey, formerly Alfa). Distilled water was used in all aqueous solutions.

Certain of the catalysts and/or carriers were subsequently treated as follows:

A total of about 22.1 grams of nickel nitrate hexahydrate (Fisher Scientific Company), about 1.7 grams of ammonium perrhenate (Strem Chemicals Inc.) and about 5.2 grams of boric acid are dissolved in 45 ml of distilled water at 65° C. A total of 22.7 ml of this solution is then added to about 55 grams of the carrier material to be evaluated, followed by calcination in air at 340° C. for about 1 hour. This material is then treated with an additional 21.8 ml of the solution, followed by calcination, and finally by 20 ml with calcination at 340° C. for three hours. The catalyst is then reduced as described above prior to evaluation. In the case of nickel formate (Johnson Matthey Electronics, formerly Alfa), the nickel and rhenium salts are dissolved in concentrated ammonium hydroxide instead of distilled water, and the boric acid is added prior to the nickel/rhenium.

| Catalyst | Carrier Material |
|---|---|
| A | UCI T-869 - silica-alumina (95:2.5), Surface area - 68 m$^2$/gm |
| B | Silica-alumina (90:10), Surface area - <1 m$^2$/gm |
| C | alpha-Alumina, Surface area - 2.8 m$^2$/gm |
| D | Norton SA-3235 - alpha-Alumina-Silica (80:20) Surface area - 11 m$^2$/gm |
| E | Norton SA-6173 - gamma-Alumina Surface area - 220 m$^2$/gm |
| F | Norton SA-6176 - gamma-Alumina Surface area - 250 m$^2$/gm |
| G | Norton SA-6175 - gamma-Alumina Surface area - 260 m$^2$/gm |
| H | Norton SN-74707 - gamma/theta-Alumina Surface area - 100 m$^2$/gm |
| I | Catalyst F hydrothermally treated to make a gamma/theta-Alumina Surface area - 116 m$^2$/gm |
| J | Catalyst F hydrothermally treated to make a theta/alpha-Alumina Surface area - 44 m$^2$/gm |
| K | Catalyst F hydrothermally treated to make a theta/alpha-Alumina Surface area - 36 m$^2$/gm |
| L | Catalyst F hydrothermally treated to make a theta/alpha-Alumina Surface area - 16 m$^2$/gm |
| M | gamma/theta-Alumina Surface area - 113 m$^2$/gm |
| N | gamma/theta-Alumina Surface area - 95 m$^2$/gm |

Catalyst A–G are included for comparative purposes. The conditions used in the examples and the results are set forth in the following Table I:

| | Example No. | | | | | |
|---|---|---|---|---|---|---|
| | 1 | 2 | 3 | 4 | 5 | 6 |
| Process Parameters | | | | | | |
| Catalyst Type | A | A | A | B | B | B |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 8.04 | 8.52 | 8.90 | 11.08 | 10.19 | 11.52 |
| Ammonia/MEA mole ratio | 10.00 | 10.00 | 10.00 | 10.00 | 10.00 | 10.00 |

| | | | | | | |
|---|---|---|---|---|---|---|
| Calculated Results | | | | | | |
| MEA conversion, % | 24.85 | 42.80 | 57.81 | 7.47 | 15.89 | 32.18 |
| EDA/PIP weight ratio | 9.20 | 4.56 | 2.42 | 15.50 | 9.74 | 4.75 |
| DETA/PIP weight ratio | 1.70 | 0.96 | 0.51 | 1.93 | 1.81 | 1.25 |
| AEEA/PIP weight ratio | 1.77 | 0.59 | 0.23 | 7.27 | 3.70 | 1.46 |
| Crude Product Composition, wt. % | | | | | | |
| EDA | 64.20 | 59.15 | 51.03 | 58.47 | 56.88 | 50.89 |
| PIP | 6.98 | 12.97 | 21.12 | 3.77 | 5.84 | 10.71 |
| DETA | 11.89 | 12.43 | 10.78 | 7.27 | 10.59 | 13.36 |
| AEEA | 12.38 | 7.62 | 4.91 | 27.45 | 21.59 | 15.59 |
| AEP | 1.36 | 2.65 | 4.96 | 1.33 | 1.05 | 1.65 |
| HEP | 0.28 | 0.49 | 0.75 | 0.00 | 0.22 | 0.44 |
| TETA | 2.06 | 2.30 | 2.06 | 0.00 | 1.48 | 2.87 |
| Others | 0.86 | 2.39 | 4.40 | 1.71 | 2.35 | 4.49 |

| | Example No. | | | | | |
|---|---|---|---|---|---|---|
| | 7 | 8 | 9 | 10 | 11 | 12 |
| Process Parameters | | | | | | |
| Catalyst Type | C | C | C | D | D | D |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 10.85 | 10.07 | 10.99 | 14.87 | 15.10 | 15.51 |
| Ammonia/MEA mole ratio | 10.00 | 10.00 | 10.00 | 10.00 | 10.00 | 10.00 |
| Calculated Results | | | | | | |
| MEA conversion, % | 9.18 | 17.39 | 30.92 | 15.54 | 28.74 | 43.87 |
| EDA/PIP weight ratio | 11.95 | 12.07 | 5.92 | 27.40 | 11.98 | 6.12 |
| DETA/PIP weight ratio | 1.55 | 1.69 | 0.97 | 3.20 | 2.13 | 1.27 |
| AEEA/PIP weight ratio | 2.32 | 1.49 | 0.54 | 4.54 | 1.86 | 0.76 |
| Crude Product Composition, wt. % | | | | | | |
| EDA | 69.25 | 71.41 | 65.23 | 75.28 | 68.42 | 62.94 |
| PIP | 5.80 | 5.91 | 11.01 | 2.75 | 5.71 | 10.28 |
| DETA | 8.98 | 9.99 | 10.73 | 8.80 | 12.16 | 13.10 |
| AEEA | 13.44 | 8.80 | 5.90 | 12.49 | 10.63 | 7.79 |
| AEP | 1.20 | 0.86 | 1.59 | 0.00 | 0.53 | 1.29 |
| HEP | 0.00 | 0.18 | 0.32 | 0.00 | 0.15 | 0.29 |
| TETA | 0.86 | 1.03 | 1.42 | 0.68 | 1.62 | 2.09 |
| Others | 0.47 | 1.81 | 3.80 | 0.01 | 0.78 | 2.22 |

| | Example No. | | | | | |
|---|---|---|---|---|---|---|
| | 13 | 14 | 15 | 16 | 17 | 18 |
| Process Parameters | | | | | | |
| Catalyst Type | E | E | E | F | F | F |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 11.67 | 11.43 | 10.94 | 13.33 | 12.88 | 14.26 |
| Ammonia/MEA mole ratio | 10.00 | 10.00 | 10.00 | 10.00 | 10.00 | 10.00 |
| Calculated Results | | | | | | |
| MEA conversion, % | 27.22 | 39.11 | 54.75 | 21.15 | 33.90 | 53.22 |
| EDA/PIP weight ratio | 12.79 | 7.26 | 3.26 | 29.94 | 18.66 | 7.47 |
| DETA/PIP weight ratio | 1.24 | 0.83 | 0.42 | 2.09 | 1.90 | 1.09 |
| AEEA/PIP weight ratio | 1.39 | 0.75 | 0.32 | 4.63 | 3.20 | 1.44 |
| Crude Product Composition, wt. % | | | | | | |
| EDA | 76.44 | 71.13 | 60.40 | 79.07 | 74.42 | 65.03 |
| PIP | 5.97 | 9.79 | 18.52 | 2.64 | 3.99 | 8.71 |
| DETA | 7.42 | 8.10 | 7.69 | 5.52 | 7.58 | 9.52 |
| AEEA | 8.33 | 7.35 | 5.88 | 12.24 | 12.76 | 12.56 |
| AEP | 0.82 | 1.50 | 3.47 | 0.28 | 0.38 | 1.27 |
| HEP | 0.30 | 0.48 | 0.76 | 0.24 | 0.33 | 0.93 |
| TETA | 0.54 | 0.69 | 0.73 | 0.00 | 0.39 | 0.84 |
| Others | 0.17 | 0.96 | 2.54 | 0.01 | 0.15 | 1.14 |

| | Example No. | | | | | |
|---|---|---|---|---|---|---|
| | 19 | 20 | 21 | 22 | 23 | 24 |
| Process Parameters | | | | | | |
| Catalyst Type | G | G | G | H | H | H |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 10.32 | 10.02 | 10.13 | 14.37 | 14.82 | 15.10 |
| Ammonia/MEA mole ratio | 10.00 | 10.00 | 10.00 | 10.00 | 10.00 | 10.00 |
| Calculated Results | | | | | | |
| MEA conversion, % | 13.80 | 24.26 | 36.33 | 26.13 | 42.97 | 61.23 |
| EDA/PIP weight ratio | 52.69 | 23.63 | 11.56 | 20.00 | 10.11 | 5.17 |
| DETA/PIP weight ratio | 2.84 | 1.88 | 1.24 | 2.97 | 1.93 | 1.21 |
| AEEA/PIP weight ratio | 11.03 | 5.88 | 3.19 | 4.29 | 1.77 | 0.86 |
| Crude Product Composition, wt. % | | | | | | |
| EDA | 77.99 | 72.23 | 66.06 | 69.64 | 65.77 | 58.53 |
| PIP | 1.48 | 3.06 | 5.71 | 3.48 | 6.51 | 11.32 |
| DETA | 4.20 | 5.75 | 7.10 | 10.36 | 12.56 | 13.70 |
| AEEA | 16.33 | 17.98 | 18.21 | 14.95 | 11.49 | 9.77 |
| AEP | 0.00 | 0.28 | 0.66 | 0.34 | 0.79 | 1.73 |
| HEP | 0.00 | 0.45 | 1.08 | 0.15 | 0.31 | 0.62 |
| TETA | 0.00 | 0.25 | 0.42 | 1.09 | 1.80 | 2.38 |
| Others | 0.00 | 0.00 | 0.75 | 0.00 | 0.76 | 1.95 |

| | Example No. | | | | | |
|---|---|---|---|---|---|---|
| | 25 | 26 | 27 | 28 | 29 | 30 |
| Process Parameters | | | | | | |
| Catalyst Type | I | I | I | J | J | J |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 9.54 | 8.32 | 10.18 | 14.57 | 13.93 | 13.55 |
| Ammonia/MEA mole ratio | 10.00 | 10.00 | 10.00 | 10.00 | 10.00 | 10.00 |
| Calculated Results | | | | | | |
| MEA conversion, % | 25.54 | 43.72 | 66.73 | 23.26 | 41.29 | 66.57 |
| EDA/PIP weight ratio | 31.29 | 15.35 | 6.32 | 20.10 | 10.77 | 4.56 |
| DETA/PIP weight ratio | 3.84 | 2.59 | 1.23 | 3.57 | 2.64 | 1.19 |
| AEEA/PIP weight ratio | 7.30 | 2.98 | 0.92 | 7.63 | 3.01 | 0.75 |
| Crude Product Composition, wt. % | | | | | | |
| EDA | 71.29 | 68.05 | 63.26 | 61.09 | 58.75 | 55.87 |
| PIP | 2.28 | 4.43 | 10.01 | 3.04 | 5.45 | 12.26 |
| DETA | 8.74 | 11.48 | 12.32 | 10.84 | 14.41 | 14.60 |
| AEEA | 16.63 | 13.22 | 9.23 | 23.20 | 16.44 | 9.24 |
| AEP | 0.16 | 0.41 | 1.41 | 0.21 | 0.54 | 1.81 |
| HEP | 0.00 | 0.23 | 0.55 | 0.00 | 0.21 | 0.50 |
| TETA | 0.73 | 1.36 | 1.84 | 1.37 | 2.70 | 3.31 |
| Others | 0.17 | 0.82 | 1.39 | 0.26 | 1.49 | 2.42 |

| | Example No. | | | | | |
|---|---|---|---|---|---|---|
| | 31 | 32 | 33 | 34 | 35 | 36 |
| Process Parameters | | | | | | |
| Catalyst Type | K | K | K | L | L | L |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 11.84 | 11.88 | 11.01 | 14.79 | 15.68 | 12.35 |
| Ammonia/MEA mole ratio | 10.00 | 10.00 | 10.00 | 10.00 | 10.00 | 10.00 |
| Calculated Results | | | | | | |
| MEA conversion, % | 23.77 | 40.01 | 66.27 | 10.43 | 23.16 | 48.99 |
| EDA/PIP weight ratio | 17.59 | 9.59 | 4.09 | 18.87 | 14.67 | 5.13 |
| DETA/PIP weight ratio | 2.87 | 1.99 | 0.94 | 2.71 | 3.33 | 1.68 |
| AEEA/PIP weight ratio | 4.51 | 1.72 | 0.45 | 15.42 | 7.78 | 1.89 |

-continued

| Crude Product Composition, wt. % | | | | | | |
|---|---|---|---|---|---|---|
| EDA | 66.32 | 64.44 | 58.24 | 48.40 | 52.48 | 47.68 |
| PIP | 3.77 | 6.72 | 14.23 | 2.57 | 3.58 | 9.30 |
| DETA | 10.84 | 13.35 | 13.39 | 6.96 | 11.91 | 15.63 |
| AEEA | 16.99 | 11.53 | 6.35 | 39.57 | 27.85 | 17.54 |
| AEP | 0.33 | 0.75 | 2.13 | 0.49 | 0.63 | 1.49 |
| HEP | 0.13 | 0.24 | 0.49 | 0.00 | 0.12 | 0.44 |
| TETA | 1.42 | 2.24 | 2.69 | 0.65 | 1.89 | 4.10 |
| Others | 0.20 | 0.73 | 2.46 | 1.36 | 1.54 | 3.81 |

| | Example No. | | | | | |
|---|---|---|---|---|---|---|
| | 37 | 38 | 39 | 40 | 41 | 42 |
| Process Parameters | | | | | | |
| Catalyst Type | M | M | M | N | N | N |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 11.97 | 11.96 | 10.79 | 11.25 | 11.46 | 11.35 |
| Ammonia/MEA mole ratio | 10.00 | 10.00 | 10.00 | 10.00 | 10.00 | 10.00 |
| Calculated Results | | | | | | |
| MEA conversion, % | 28.61 | 46.69 | 67.66 | 30.19 | 44.08 | 68.62 |
| EDA/PIP weight ratio | 19.47 | 12.98 | 5.95 | 17.94 | 12.36 | 4.37 |
| DETA/PIP weight ratio | 2.57 | 2.35 | 1.35 | 2.21 | 1.83 | 0.89 |
| AEEA/PIP weight ratio | 4.08 | 2.38 | 0.99 | 2.73 | 1.68 | 0.56 |
| Crude Product Composition, wt. % | | | | | | |
| EDA | 68.94 | 66.82 | 59.94 | 73.37 | 70.86 | 59.39 |
| PIP | 3.54 | 5.15 | 10.07 | 4.09 | 5.73 | 13.60 |
| DETA | 9.11 | 12.11 | 13.58 | 9.04 | 10.50 | 12.16 |
| AEEA | 14.44 | 12.27 | 10.00 | 11.18 | 9.61 | 7.59 |
| AEP | 0.64 | 0.55 | 1.46 | 0.50 | 0.68 | 2.26 |
| HEP | 0.41 | 0.27 | 0.58 | 0.20 | 0.28 | 0.66 |
| TETA | 1.19 | 1.67 | 2.42 | 0.53 | 1.10 | 1.98 |
| Others | 1.73 | 1.15 | 1.95 | 1.09 | 1.23 | 2.36 |

The examples in Table I show the effect of various carriers impregnated with nickel, rhenium, and boron using a method similar to that disclosed in U.S. Pat. No. 4,123,462. Catalyst A, a preferred silica/alumina (UCI T-869) of U.S. Pat. No. 4,123,462, was prepared as a comparative example. Catalyst B shows a predominantly alpha alumina mixed with silica. Catalysts C. and D show aluminas which are predominately alpha, which are not effective carriers. Catalysts E, F, and G show gamma-aluminas which are not useful transitional aluminas for the present invention, as they do not provide both good activity and selectivity. Catalysts H, M, and N show gamma/theta aluminas, which provide both high activity and selectivity. Catalyst I, J, K and L show a gamma-alumina (Catalyst F) hydrothermally treated to provide gamma/theta and theta/alpha alumina carriers, at various surface areas and porosities, which are effective carriers for Ni—Re catalysts. At progressively higher hydrothermal treatments, the catalyst becomes more alpha rich (as indicated by decreasing surface area) and its effectiveness as a carrier becomes diminished (Catalyst L).

The examples in the following Table II show the effectiveness of various gamma/theta alumina carriers for Ni—Re catalyst, and the effect of nickel to rhenium atom ratios on gamma/theta alumina carriers. The following metals solutions were used to prepare the reductive amination catalyst on the designated transitional alumina carriers using the procedures described above:

| Catalyst | Carrier | Metal Salts |
|---|---|---|
| O | 55 grams of UCI T-869 - silica-alumina (95:2.5); Surface area - 68 m²/gm | 22.18 grams of nickel nitrate hexahydrate; 1.69 grams of ammonium perrhenate |
| P | 55 grams of gamma/theta-Alumina; Surface area - 113 m²/gm | 14.13 grams of nickel formate; 1.72 grams of ammonium perrhenate (Ni:Re = 11.6:1) |
| Q | 55 grams of gamma/theta-Alumina; Surface area - 113 m²/gm | 18.9 grams of nickel acetate; 1.7 grams of ammonium perrhenate (Ni:Re = 11.6:1) |
| R | 55 grams of gamma/theta-Alumina; Surface area - 113 m²/gm | 14.14 grams of nickel formate; 0.42 grams of ammonium perrhenate (Ni:Re = 48:1) |
| S | 55 grams of gamma/theta-Alumina; Surface area - 113 m²/gm | 14.09 grams of nickel formate; 0.18 grams of ammonium perrhenate (Ni:Re = 116:1) |
| T | 55 grams of gamma/theta-Alumina; Surface area - 113 m²/gm | 14.16 grams of nickel formate; 0.09 grams of ammonium perrhenate (Ni:Re = 232:1) |
| U | 55 grams of gamma/theta Alumina; Surface area 80 m²/gm | 18.94 grams of nickel acetate; 0.6 grams of ammonium perrhenate |
| V | 55 grams of gamma/theta Alumina; Surface area - 80 m²/gm | 22.17 grams of nickel nitrate; 0.62 grams of ammonium perrhenate |
| W | 55 grams of Norton SN-74707 - gamma/theta-Alumina; Surface area - 100 m²/gm | 22.15 grams of nickel nitrate; 0.6 grams of ammonium perrhenate |

| | Example No. | | | | | |
|---|---|---|---|---|---|---|
| | 43 | 44 | 45 | 46 | 47 | 48 |
| Process Parameters | | | | | | |
| Catalyst Type | O | O | O | P | P | P |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 14.60 | 15.65 | 14.93 | 13.36 | 12.47 | 13.33 |
| Ammonia/MEA mole ratio | 10.00 | 10.00 | 10.00 | 10.00 | 10.00 | 10.00 |
| Calculated Results | | | | | | |
| MEA conversion, % | 16.41 | 30.88 | 53.38 | 32.98 | 49.90 | 72.69 |
| EDA/PIP weight ratio | 21.25 | 9.92 | 3.68 | 14.41 | 8.50 | 3.84 |
| DETA/PIP weight ratio | 2.31 | 1.50 | 0.74 | 3.01 | 2.02 | 0.99 |
| AEEA/PIP weight ratio | 3.59 | 1.43 | 0.47 | 5.42 | 2.08 | 0.67 |
| Crude Product Composition, wt. % | | | | | | |
| EDA | 74.33 | 69.41 | 57.59 | 57.07 | 58.81 | 53.36 |
| PIP | 3.50 | 7.00 | 15.66 | 3.96 | 6.92 | 13.90 |
| DETA | 8.06 | 10.51 | 11.56 | 11.94 | 13.94 | 13.73 |
| AEEA | 12.55 | 9.98 | 7.36 | 21.48 | 14.36 | 9.33 |
| AEP | 0.95 | 1.31 | 3.19 | 0.96 | 1.11 | 2.45 |
| HEP | 0.00 | 0.26 | 0.64 | 0.27 | 0.38 | 0.81 |
| TETA | 0.61 | 1.10 | 1.78 | 2.05 | 2.77 | 3.15 |
| Others | 0.00 | 0.42 | 2.23 | 2.26 | 1.71 | 3.27 |

| | Example No. | | | | | |
|---|---|---|---|---|---|---|
| | 49 | 50 | 51 | 52 | 53 | 54 |
| Process Parameters | | | | | | |
| Catalyst Type | Q | Q | Q | R | R | R |
| Catalyst Weight, gm. | 50 | 50 | 50 | 50 | 50 | 50 |
| Temperature, °C. | 160 | 170 | 180 | 160 | 170 | 180 |

13

-continued

| | | | | | | |
|---|---|---|---|---|---|---|
| Pressure, psig | 1814 | 1814 | 1814 | 1814 | 1814 | 1814 |
| MEA SV, gmol/hr/kgcat | 13.61 | 13.96 | 12.11 | 14.69 | 10.21 | 12.14 |
| Ammonia/MEA mole ratio | 10.00 | 10.00 | 10.00 | 10.00 | 10.00 | 10.00 |
| Calculated Results | | | | | | |
| MEA conversion, % | 25.93 | 42.41 | 65.49 | 44.44 | 64.14 | 71.47 |
| EDA/PIP weight ratio | 19.48 | 13.59 | 6.08 | 6.86 | 3.79 | 3.24 |
| DETA/PIP weight ratio | 2.89 | 2.88 | 1.41 | 1.63 | 0.84 | 0.75 |
| AEEA/PIP weight ratio | 6.33 | 3.96 | 1.27 | 2.76 | 0.87 | 0.68 |
| Crude Product Composition, wt. % | | | | | | |
| EDA | 63.54 | 60.36 | 57.83 | 49.06 | 53.04 | 51.26 |
| PIP | 3.26 | 4.44 | 9.51 | 7.15 | 13.99 | 15.81 |
| DETA | 9.41 | 12.80 | 13.44 | 11.63 | 11.81 | 11.89 |
| AEEA | 20.64 | 17.61 | 12.05 | 19.74 | 12.23 | 10.71 |
| AEP | 1.01 | 0.82 | 1.46 | 1.55 | 2.43 | 2.92 |
| HEP | 0.23 | 0.30 | 0.66 | 0.79 | 0.91 | 1.12 |
| TETA | 1.02 | 1.85 | 2.51 | 2.50 | 2.44 | 2.52 |
| Others | 0.89 | 1.83 | 2.54 | 7.58 | 3.15 | 3.78 |

| | Example No. | | | | | |
|---|---|---|---|---|---|---|
| | 55 | 56 | 57 | 58 | 59 | 60 |
| Process Parameters | | | | | | |
| Catalyst Type | S | S | S | T | T | T |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 15.69 | 12.87 | 13.76 | 14.08 | 13.98 | 13.91 |
| Ammonia/MEA mole ratio | 10.00 | 10.00 | 10.00 | 10.00 | 10.00 | 10.00 |
| Calculated Results | | | | | | |
| MEA conversion, % | 11.56 | 25.07 | 42.50 | 10.63 | 16.34 | 24.50 |
| EDA/PIP weight ratio | 47.92 | 20.49 | 8.85 | 38.75 | 35.22 | 17.43 |
| DETA/PIP weight ratio | 3.66 | 2.67 | 1.60 | 2.65 | 2.83 | 1.92 |
| AEEA/PIP weight ratio | 22.96 | 9.11 | 3.77 | 17.28 | 15.53 | 9.59 |
| Crude Product Composition, wt. % | | | | | | |
| EDA | 61.02 | 59.21 | 54.56 | 62.46 | 61.92 | 55.97 |
| PIP | 1.27 | 2.89 | 6.17 | 1.61 | 1.76 | 3.21 |
| DETA | 4.66 | 7.72 | 9.88 | 4.27 | 4.97 | 6.15 |
| AEEA | 29.23 | 26.32 | 23.25 | 27.86 | 27.30 | 30.80 |
| AEP | 1.67 | 0.98 | 1.08 | 1.68 | 1.09 | 0.98 |
| HEP | 0.00 | 0.34 | 0.89 | 0.27 | 0.22 | 0.63 |
| TETA | 0.00 | 0.73 | 1.48 | 0.00 | 0.00 | 0.52 |
| Others | 2.15 | 1.80 | 2.70 | 1.85 | 2.74 | 1.75 |

| | Example No. | | | | | |
|---|---|---|---|---|---|---|
| | 61 | 62 | 63 | 64 | 65 | 66 |
| Process Parameters | | | | | | |
| Catalyst Type | U | U | U | V | V | V |
| Catalyst Weight, gm. | 50 | 50 | 50 | 50 | 50 | 50 |
| Temperature, °C. | 160 | 170 | 180 | 160 | 170 | 180 |
| Pressure, psig | 1814 | 1814 | 1814 | 1814 | 1814 | 1814 |
| MEA SV, gmol/hr/kgcat | 11.31 | 10.42 | 10.56 | 9.48 | 9.90 | 8.96 |
| Ammonia/MEA mole ratio | 10.00 | 10.00 | 10.00 | 10.00 | 10.00 | 10.00 |
| Calculated Results | | | | | | |
| MEA conversion, % | 24.35 | 46.06 | 68.62 | 33.20 | 52.78 | 60.48 |
| EDA/PIP weight ratio | 13.46 | 8.12 | 3.61 | 6.68 | 3.50 | 3.39 |
| DETA/PIP weight ratio | 2.37 | 2.04 | 0.94 | 1.46 | 0.94 | 0.87 |
| AEEA/PIP weight ratio | 5.53 | 2.28 | 0.66 | 2.10 | 0.68 | 0.64 |
| Crude Product Composition, wt. % | | | | | | |
| EDA | 57.17 | 56.48 | 52.19 | 55.30 | 50.66 | 50.58 |
| PIP | 4.25 | 6.95 | 14.45 | 8.27 | 14.49 | 14.93 |
| DETA | 10.05 | 14.19 | 13.53 | 12.07 | 13.60 | 12.98 |
| AEEA | 23.48 | 15.84 | 9.50 | 17.34 | 9.79 | 9.53 |
| AEP | 0.41 | 0.96 | 2.50 | 1.46 | 3.08 | 2.59 |
| HEP | 0.21 | 0.46 | 0.95 | 0.52 | 0.97 | 1.08 |

14

-continued

| | | | | | | |
|---|---|---|---|---|---|---|
| TETA | 1.75 | 2.92 | 3.38 | 2.49 | 3.72 | 3.20 |
| Others | 2.68 | 2.18 | 3.49 | 2.56 | 3.70 | 5.11 |

| | Example No. | | |
|---|---|---|---|
| | 67 | 68 | 69 |
| Process Parameters | | | |
| Catalyst Type | W | W | W |
| Catalyst Weight, gm. | 50 | 50 | 50 |
| Temperature, °C. | 160 | 170 | 180 |
| Pressure, psig | 1814 | 1814 | 1814 |
| MEA SV, gmol/hr/kgcat | 13.44 | 13.10 | 12.95 |
| Ammonia/MEA mole ratio | 10.00 | 10.00 | 10.00 |
| Calculated Results | | | |
| MEA conversion, % | 26.53 | 45.43 | 66.50 |
| EDA/PIP weight ratio | 14.23 | 7.25 | 3.22 |
| DETA/PIP weight ratio | 2.81 | 1.88 | 0.90 |
| AEEA/PIP weight ratio | 5.73 | 2.34 | 0.71 |
| Crude Product Composition, wt. % | | | |
| EDA | 57.20 | 53.77 | 48.53 |
| PIP | 4.02 | 7.41 | 15.07 |
| DETA | 11.28 | 13.91 | 13.55 |
| AEEA | 23.05 | 17.33 | 10.77 |
| AEP | 0.39 | 1.02 | 2.73 |
| HEP | 0.25 | 0.55 | 1.11 |
| TETA | 2.00 | 3.29 | 3.86 |
| Others | 1.81 | 2.71 | 4.36 |

Catalysts P, U, V and W show improved performance for gamma/theta alumina carriers compared to Catalyst O, the UCI T-869 silica-alumina carrier disclosed in U.S. Pat. No. 4,123,462. Catalysts Q, R, S and T show useful ranges of Ni/Re atom ratios with gamma/theta alumina carriers.

What is claimed is:

1. A method for reductive amination of MEA comprising contacting MEA and ammonia with a solid reductive amination catalyst comprising at least one catalytically effective reduction amination metal incorporated with a transitional alumina carrier selected from the group consisting of delta, theta, gamma/theta, delta/theta, and theta/alpha alumina phases, and mixtures thereof, under reductive amination conditions sufficient to provide a higher ratio of acyclic to cyclic products when compared to a similar catalyst not containing said transitional aluminas.

2. The method of claim 1 wherein the catalytically effective reduction amination metal or metals is selected from the group consisting of nickel, rhenium, cobalt, rhodium, iridium, ruthenium, zinc, palladium and platinum.

3. The method of claim 2 wherein the catalytically effective reductive amination metals are nickel and rhenium, having an atom ratio of nickel to rhenium in the range of from about 1:1 to about 200:1.

4. The method of claim 3 wherein the atom ratio of nickel to rhenium is in the range of from about 5:1 to 100:1.

5. The method of claim 4 wherein the atom ratio of nickel to rhenium is in the range of from about 10:1 to 50:1.

6. The method of claim 1 wherein the total reductive amination metal content is in the range of from about 1 to 30 percent by weight of the carrier.

7. The method of claim 6 wherein the total reductive amination metal content is in the range of from about 5 to 15 percent by weight of the carrier.

8. The method of claim 1 wherein the catalyst further comprises boron.

* * * * *

UNITED STATES PATENT AND TRADEMARK OFFICE
CERTIFICATE OF CORRECTION

PATENT NO. : 5,750,790
DATED : May 12, 1998
INVENTOR(S) : S.W. King

It is certified that error appears in the above-identified patent and that said Letters Patent is hereby corrected as shown below:

Col. 2, line 39 "7500°" should be "750°".

Col. 5, line 40 "rhenilium" should be "rhenium".

Signed and Sealed this

Eleventh Day of August 1998

*Attest:*

BRUCE LEHMAN

*Attesting Officer*     *Commissioner of Patents and Trademarks*